United States Patent [19]

Dattagupta et al.

[11] Patent Number: 5,294,534
[45] Date of Patent: Mar. 15, 1994

[54] AMPLIFICATION METHOD FOR POLYNUCLEOTIDE ASSAYS

[75] Inventors: Nanibhushan Dattagupta, Orange; Elizabeth C. Sullivan, Stamford, both of Conn.

[73] Assignee: Miles, Inc., Elkhart, Ind.

[21] Appl. No.: 744,548

[22] Filed: Aug. 13, 1991

[51] Int. Cl.$^5$ .................. C12Q 1/44; C12Q 1/68
[52] U.S. Cl. ........................... 435/6; 435/18; 435/91.2; 435/199; 935/17; 935/78
[58] Field of Search ............ 435/6, 18, 91, 199, 435/810; 935/17, 77, 78

[56] References Cited

U.S. PATENT DOCUMENTS

| | | | |
|---|---|---|---|
| 4,683,195 | 7/1987 | Mullis et al. | 435/6 |
| 4,775,619 | 10/1988 | Urdea | 435/6 |

FOREIGN PATENT DOCUMENTS

| | | |
|---|---|---|
| 0142299 | 5/1985 | European Pat. Off. |
| 0300796 | 1/1989 | European Pat. Off. |
| 0360940 | 4/1990 | European Pat. Off. |
| 8912697 | 12/1989 | PCT Int'l Appl. |
| 9009455 | 8/1990 | PCT Int'l Appl. |

OTHER PUBLICATIONS

A Restriction Enzyme Can Digest Partially Double Stranded DNA Sites, Nanibhushan Dattagupta and Elizabeth Carlson-Sullivan (21 pages).

*Primary Examiner*—Robert A. Wax
*Assistant Examiner*—Rebecca Prouty
*Attorney, Agent, or Firm*—Sprung Horn Kramer & Woods

[57] ABSTRACT

A process for detecting a nucleic acid sequence in a sample comprising:
(1) treating said sample under hybridization conditions with an oligonucleotide that lacks a recognition site for enzyme digestion;
(2) extending the hybridization product from step (1) by adding polymerase and NTPs to create on the oligonucleotide strand a recognition site for enzyme digestion;
(3) treating the product of step (2) with labeled probe, which is immobilized or immobilizable and which contains a recognition site for enzyme digestion that is completely or partially complementary to the recognition site for enzyme digestion on the oligonucleotide strand, under conditions that the oligonucleotide strand becomes hybridized to the labeled probe;
(4) digesting the separated hybridization product of step (3) with restriction endonuclease; and
(5) detecting the separated label which is released in solution. A kit for use in detecting the presence of a nucleic acid sequence in a sample, which comprises (1) labeled probe, (2) an oligonucleotide sequence for extension, and (3) a restriction endonuclease is also disclosed.

1 Claim, No Drawings

AMPLIFICATION METHOD FOR POLYNUCLEOTIDE ASSAYS

BACKGROUND OF THE INVENTION

1. Field of the Invention

The ability to synthesize oligonucleotide sequences at will and to clone polynucleotide sequences prepared by synthetic procedures or obtained from naturally occurring sources has greatly expanded the opportunities for detecting the presence of specific sequences in an extended oligonucleotide sequence. Interest in the specific sequences may involve the diagnosis of the presence of pathogens, the determination of the presence of alleles, the presence of lesions in a host genome, the detection of a particular mRNA or the monitoring of a modification of a cellular host, to mention only a few opportunities. While the use of antibodies to perform assays diagnostic of the presence of various antigens in samples has seen an explosive expansion in techniques and protocols since the advent of radioimmunoassay, there has been until recently no parallel activity in the area of the DNA probes. Therefore, for the most part, detection of sequences has involved various hybridization techniques requiring the binding of a polynucleotide sequence to a support and employing a radiolabeled probe.

In view of the increasing capability to produce oligonucleotide sequences in large amounts in an economical way, the attention of investigators will be directed to providing for simple, accurate and efficient techniques for detecting specific oligonucleotide sequences. Desirably, these techniques will be rapid, minimize the opportunity for technician error, be capable of automation, and allow for simple and accurate methods of detection. Toward this end, there have already been efforts to provide for means to label oligonucleotide probes with labels other than radioisotopes and for improving the accuracy of transfer of DNA sequences to a support from a gel, as well as improved methods for derivatizing oligonucleotide to allow for binding to a label. There continues to be a need for providing new protocols which allow for flexibility in detecting DNA sequences of interest in a variety of situations where the DNA may come from diverse sources.

2. Description of the Related Art

Meinkoth and Wahl, Anal. Biochemistry (1984) 138:267-284, provide an excellent review of hybridization techniques. Leary et al., Proc. Natl. Acad. Sci. USA (1983) 80:4045-4049, describe the use of biotinylated DNA in conjunction with an avidin-enzyme conjugate for detection of specific oligonucleotide sequences. Ranki et al., Gene (1983) 21:77-85, describe what they refer to as a "sandwich" hybridization for detection of oligonucleotide sequences. Pfeuffer and Helmrich, J. of Biol. Chem. (1975) 250:867-876, describe the coupling of guanosine-5'-O-(3-thiotriphosphate) to Sepharose 4B. Bauman, et al., J. of Histochem. and Cytochem. (1981) 29:227-237, describe the 3'-labeling of RNA with fluorescers. PCT Application WO/8302277 describes the addition to DNA fragments of modified ribonucleotides for labeling and methods for analyzing such DNA fragments. Renz and Kurz, Nucl. Acids Res. (1984) 12:3435-3444, describe the covalent linking of enzymes to oligonucleotides. Wallace, DNA Recombinant Technology (Woo, S., Ed.) CRC Press, Boca Raton, Fla., provides a general background of the use of probes in diagnosis. Chou and Merigan, N. Eng. J. of Med. (1983) 308:921-925, describe the use of a radioisotope labeled probe for the detection of CMV. Methods in Enzymol., 34B, 24 (1974) 30-59, describes procedures for linking to polyamides, while Parikh, et al., Methods in Enzymol., 34B, 24 (1974) 77-102, describe coupling reactions with agarose. Alwine, et al., Proc. Natl. Acad. Sci. USA (1977) 74:5350-5354, describe a method of transferring oligonucleotides from gels to a solid support for hybridization. Chu, et al., Nucl. Acids Res. (1983) 11:6513-6529, describe a technique for derivatizing terminal nucleotides. Ho, et al., Biochemistry (1981) 20:64-67, describe derivatizing terminal nucleotides through phosphate to form esters. Ashley and MacDonald, Anal. Biochem. (1984) 140:95-103, report a method for preparing probes from a surface bound template. These references which describe techniques are incorporated herein by reference in support of the preparation of labeled oligonucleotides.

EP 360940 describes methods for the detection of specific nucleotide sequences employing a solid support, at least one label, and hybridization involving a sample and a labeled probe, where the presence or absence of duplex formation results in the ability to modify the spatial relationship between the support and label(s). Exemplary of the technique is to provide a cleavage site between the label and support through duplexing of a labeled probe and sample DNA, where the duplex is bound to a support. The cleavage site may then be cleaved resulting in separation of the support and the label(s). Detection of the presence or absence of the label may then proceed in accordance with conventional techniques, e.g., by measuring the amount of label freed into a surrounding medium.

SUMMARY OF THE INVENTION

The present invention relates generally to a simple method for using an immobilized probe and release of the hybrid via restriction digestion to detect a target oligonucleotide sequence.

In one embodiment of the invention, the method generally comprises the following steps:

(1) treating said sample under hybridization conditions with an oligonucleotide that lacks a recognition site for enzyme digestion;

(2) extending the hybridization product from step (1) by adding polymerase and NTPs to create on the oligonucleotide strand a recognition site for enzyme digestion;

(3) treating the product of step (2) with labeled probe, which is immobilized or immobilizable and which contains a recognition site for enzyme digestion that is completely or partially complementary to the recognition site for enzyme digestion on the oligonucleotide strand, under such conditions that the oligonucleotide strand becomes hybridized to the labeled probe;

(4) digesting the hybridization product of step (3) with restriction endonuclease; and (5) detecting the separated label which is released in solution.

The present method is based partly on the discovery that certain restriction endonucleases, e.g., Alu I, can digest partially double stranded deoxyoligonucleotides with incomplete recognition sites.

The present method allows the detection of a primary nucleotide sequence even if there is only a low concentration of the nucleic acid and even if there is only a low presence of the sequence of interest in the nucleic acid. The single stranded pattern of the oligonucleotide extended by NTPs is transferred from the nucleic acid to an immobilized or immobilizable labeled probe, which is then digested to form a detectable label. Extension step (2) repeats itself so long as conditions are maintained, e.g., thermocyclina, polymerase and the requisite NTPs are readily available. Surprisingly, the digestion step (4) also repeats itself automatically under specific, but flexible conditions. After an initial digestion, the residual duplex will split to form a single stranded pattern comprising the digested oligonucleotide, which is then available to hybridize to another complementary sequence to form another duplex that can then be digested, and so on.

The present invention also relates generally to a kit for use in detecting the presence of a nucleic acid sequence in a sample, the kit comprising (1) labeled probe, (2) an oligonucleotide sequence for extension, and (3) a restriction endonuclease.

DETAILED DESCRIPTION OF THE INVENTION

The sample will comprise a nucleic acid sequence containing a sequence of interest. The sample will be treated with an oligonucleotide sequence. The treatment of the sample with the oligonucleotide sequence will be under conditions such that duplex formation occurs between complementary sequences.

The subject method can be used for the detection of nucleic acid sequences, either DNA or RNA, in a wide variety of situations. One important area of interest is the detection of pathogens, viruses, bacteria, fungi, protozoa, or the like, which can infect a particular host. Another area of interest is the detection of alleles, mutations, or lesions present in the genome of a host, such as involved in amniocentesis, genetic counseling, host sensitivity or susceptibility determinations, and monitoring of cell populations. A third area of interest is the determination of the presence of RNA for such diverse reasons as monitoring transcription, detecting RNA viruses, differentiating organisms through unexpressed RNA, and the like. Other areas of interest, which are intended to be illustrative, but not totally inclusive, include monitoring modified organisms for the presence of extrachromosomal DNA or integrated DNA, amplifications of DNA sequences, the maintenance of such sequences, and the analysis of environmental samples, e.g., waste water, soil samples, and the like.

The physiological samples may be obtained from a wide variety of sources as is evident from the varied purposes for which the subject method may be used. Sources may include various physiological fluids, such as excreta, e.g., stool, sputum, urine, saliva, etc.; plasma, blood, serum, ocular lens fluids, spinal fluid, lymph, and the like. The sample may be used without modification or may be modified by expanding the sample, cloning, or the like, to provide an isolate, so that there is an overall enhancement of the DNA or RNA and reduction of extraneous RNA or DNA. Viruses may be plated on a lawn of compatible cells, so as to enhance the amount of viral DNA; clinical isolates may be obtained by the sample being streaked or spotted on a nutrient agar medium and individual colonies assayed; or the entire sample introduced into a liquid broth and the cells selectively or nonselectively expanded. The particular manner in which the sample is treated will depend on the nature of the sample, the nature of the DNA or RNA source, the length of nucleic acid sequence of interest which is anticipated as being present as compared to the total amount of nucleic acid present, as well as the sensitivity of the protocol and label being employed.

The nature of the oligonucleotide can vary greatly. However, the oligonucleotide sequence will usually be complementary to the nucleic acid sequence of interest in the sample. Yet, the oligonucleotide sequence need not be completely complementary to the nucleic acid sample. The oligonucleotide can be 3 to 100 nucleotides in length, preferably 10 to 40 nucleotides in length.

The hybridization reaction between the sample and the oligonucleotide will be carried out according to procedures well known to those of ordinary skill in the art. See, e.g., J. Sambrook et al., *Molecular Cloning*, 2nd edit., Cold Spring Harbor Press (1989) (for example, hybridization will in general be effected by treating the sample with the oligonucleotide under appropriate buffer and temperature parameters as described better in the text.)

After the oligonucleotide has been hybridized to the sample, polymerase and NTPs will be added to the hybridization product under conditions so as to extend the duplex to the point wherein a recognition site for enzyme digestion is added. A "recognition site for enzyme digestion" should be understood to mean in the case of a hydridization product a site either between the duplex termini or at one duplex terminus which comprises the bases that are regarded in the art as being necessary for digestion, given the particular restriction endonuclease involved. In the case of an oligonucleotide strand or labeled probe, a "recognition site for enzyme digestion" should be understood to mean a site either between the strand terminus or at one strand termini which comprises the bases that would be necessary for digestion were the strand hydridized to its complete or partial complementary strand, given the particular restriction endonuclease involved.

Suitable polymerases for the extension step include, but are not limited to DNA polymerase I, Klenow, Taq polymerase, and reverse transcriptase. In a preferred embodiment, Tag polymerase is used as the polymerase.

The extension step will be carried out under conditions conducive to the formation of a recognition site for enzyme digestion. Such conditions will, of course, vary depending on the particular hybridization product involved. Nevertheless, in general, the techniques for accomplishing such an extension, including the manipulation of conditions so as to be conducive to accomplishing such an extension, are within the skill of the ordinary practitioner in the art. For example, see J. Sambrook et al., *Molecular Cloning*, 2nd edit., Cold Spring Harbor Press (1989). Preferably, the extension step will be carried out under appropriate buffer and temperature conditions.

Once the hybridization product has been extended to create a recognition site for enzyme digestion, the extended hybridization product will be treated with a labeled probe, which is either immobilized or immobilizable. The single stranded pattern of the oligonucleotide sequence extended by NTPs will, thereby, be transferred to the immobilized or immobilizable labeled probe. The conditions for effecting this transfer are well known to those of ordinary skill in the art, the important requirement being that the hybrid formed be stable.

The detection probe will usually constitute a polynucleotide sequence of at least 10 bases and not more than 10K bases. Preferably, the probe will contain 10 to 100 bases. There will be a region in the probe completely or partially complementary with the oligonucleotide sequence extended by NTPs. This region will normally constitute at least 3 bases, preferably at least 10 bases.

The label is to be joined to the probe through a link which is retained during the assay. A wide variety of labels may be employed, where the label may provide for a detectable signal or means for obtaining a detectable signal. Such labels are well known in the art.

Labels therefore include such diverse substituents as ligands, radioisotopes, enzymes, fluorescers, chemiluminescers, enzyme suicide inhibitors, enzyme cofactors, enzyme substrates, or other substituents which can provide, either directly or indirectly, a detectable signal.

The probe will either already be immobilized to the support at the time the extended hybridization product is treated with the probe or the probe will thereafter be immobilizable to a support.

The support may include, for example, magnetic particles, paper supports, other 3D particles, cellulose, sephadex, latex, and sepharose.

To ensure binding of the probe to the support throughout the assay, a variety of different techniques may be employed. For example, use may be made of avidin-biotin interactions, covalent bonding, etc.

Preferably, the probe will be biotinylated, which can react with the avidinylated support, creating an immobilized probe or the oligonucleotide can be covalently linked to a solid support.

After hybridization of the extended oligonucleotide sequence to the labeled probe, the labeled probe will be digested with a restriction endonuclease, which recognizes the double stranded site.

Where the probe is not yet immobilized to a support, the immobilization will be carried out either before or after enzyme digestion. Preferably, such immobilization is carried out before digestion.

The restriction endonuclease will be one that recognizes the recognition site for digestion and cuts the duplex at that site. Examples of restriction endonucleases that recognize such restriction sites are well known, but Alu I is preferred.

Digestion will be effected by techniques well known in the art. See, e.g., J. Sambrook et al., *Molecular Cloning*, 2nd edit., Cold Spring Harbor Press (1989). For example, digestion will be effected by combining the restriction endonuclease with the labeled probe as described in the instant examples, e.g., in the presence of 40 mM Tris pH 8, 10 mM MgCl$_2$, 10 mM NaCl, 1 mM DTT, 50 µg/ml BSA at 37° C. for 30'. In a preferred embodiment, digestion will be effected under buffer and conditions conducive to that of the given enzyme.

Once digestion is completed, the probe will be immobilized if the probe has not been immobilized already. In either case, the support will next be separated from the supernatant and washed free of at least substantially all of the non-specifically bound label.

Various protocols may then be employed, where normally the supernatant may be assayed for the presence of the label, although in some instances the support may also be measured. Protocols and reagents may be employed where a physical separation of the support from the supernatant may or may not be required. Exemplary protocols and reagents are set forth in EP-A 0 360 940.

Under appropriate conditions, the support bound duplex will cleave thereby yielding the oligonucleotide sequence extended by NTPs. If conditions are favorable, the extended oligonucleotide will hybridize to another labeled probe molecule, thereby again forming a recognition site for restriction endonuclease digestion. Digestion of this new duplex will follow again initiating release of the digested extended oligonucleotide and also labeled oligonucleotide. This "cycling" sequence will repeat automatically as long as undigested labeled probe is available and conditions are maintained. This cycling phenomenon is surprising and, moreover, advantageous since a given amount of extended oligonucleotide results in amplification of the release of the label into the surrounding medium.

The kit will include the items mentioned previously. However, it is also possible to include reagents for extension of the oligonucleotide sequence and/or reagents for detecting the separated label.

The invention is demonstrated further by the following illustrative examples.

EXAMPLE 1

A. Material and Methods

Oligonucleotides were synthesized using an automated Applied Biosystem 380B oligonucleotide synthesizer. Oligonucleotides were gel purified and electroeluted. Oligonucleotides were isotopically labelled with 32P using a T4 polynucleotide kinase and ATP.

Kinased oligonucleotides were purified by ethanol precipitation. Alu I restriction enzyme was purchased from Pharmacia and Boehringer Mannheim. An analytical denaturing protein gel of the enzyme from these two suppliers indicates similar patterns of multiple bands. Protein content per unit activity is greater in the Pharmacia product than in the Boehringer Mannheim material. Digestion with Alu I restriction enzyme was done in a buffer containing 40 mM Tris pH 8, 10 mM MgCl$_2$, 10 mM NaCl, 1 mM DTT, and 50 µg/ml BSA. A typical mixture contained 9.5 µmoles of a labeled oligonucleotide and 1.2 µmoles of unlabeled complementary oligonucleotide in 25 microliters. Five units of enzyme was added and the mixture was incubated in a 37° C. waterbath for 30 minutes. (One unit of Alu I will digest 1 µg λ DNA in 50 µl assay buffer in 1 hour at 37° C.) After the digestion reaction, the sample was analyzed on a 20% denaturing polyacrylamide gel followed by autoradiography.

B. Digestion of Partially Double Stranded Sites

Deoxyoligonucleotide sequences BRECL 1 through 10 and BRALU 1 were hybridized to a 32P labeled complementary sequence COMBR10 and digested with five units of Alu I at 37° C. for 30 minutes. Autoradiography of the gel clearly shows that BRECL 2 can initiate the restriction digestion. A surprising observation is that BRECL 4, which contains a complete site, is not very efficient in the process. Further, elongated sequences provide a good digestion site for the enzyme. The efficiency of BRECL 2 seemed to improve when a longer sequence (EX3ECL1) is used as the complementary strand.

When the same experiment was done with the complementary sequence, it was found that COMPBR 3 is very efficient in providing a complementary digestible sequence.

The recognition of a partial sequence needs one strand containing the complete . . . AGCT . . . recognition sequence. The autoradiograph clearly shows that a partial or completely double stranded . . . AGC . . . sequence is not digested by Alu I.

C. Cycling

Although Alu I does not digest single stranded DNA, a cycling digestion reaction is possible because Alu I recognizes a partial sequence. An analysis of the time dependence of the digestion of a 32P labeled oligonucleotide with a constant amount of a complementary sequence using Alu I shows that Alu I digests more than a five-fold excess of the expected amount.

D. Supplier Variation

Enzymes obtained from different suppliers show similar digestion properties of Alu I restriction enzyme. Since these unusual properties of Alu I were observed, analysis of the enzyme in terms of its protein content was warranted. Pharmacia enzyme shows more protein per unit activity and also multiple bands. The Boehringer Mannheim enzyme apparently looks cleaner in terms of other components. Although the enzyme preparations from different suppliers show some qualitative differences, their digestion properties were indistinguishable.

EXAMPLE 2

A. Materials and Methods

3'-derivatization was carried out with terminal deoxynucleotidyl transferase (Pharmacia). Digoxigenin labeled dUTP was obtained from Boehringer Mannheim. Steptavidin coated magnetic particles were purchased from Dynal.

B. Experimental

5'-biotinylated-3'-digoxigenin labeled probe was hybridized with a complementary target sequence. The hybrid was captured onto streptavidin coated particles. The captured hybrid was reacted with an anti-digoxigenin antibody conjugated to alkaline phosphatase. The enzyme complexed hybrid was then digested with Alu I restriction enzyme in 40 mM Tris pH 8, 10 mM MgCl$_2$, 10 mM NaCl, 1 mM DTT, 50 µg/ml BSA. The released product was analyzed via the enzyme activity. The alkaline phosphatase detection was done either in a luminometer (LKB 1251) using a photogene kit (Life Technologies, Inc.) or on nitrocellulose paper using nitroblue tetrazolium/bromo-chloroindolyl phosphate as substrate.

As controls, identical experiments with biotinylated oligonucleotides lacking digoxigenin labels were used as probes. It was observed that the presence of mercaptoethanol or dithiothreitol type compounds, which are essential for efficient restriction digestion, interferes with the alkaline phosphatase assay. In order to avoid that problem, the solution after digestion was spotted onto a nitrocellulose paper to adsorb proteins or solid preswollen saphadex was added to the digestion solution to adsorb any thio type compound.

EXAMPLE 3

BRALU1 is a synthetic oligonucleotide (22 mer) representing a portion of the gene of the major outer membrane protein sequence of Chlamydia trachomitis. In the presence of the following components, BRALU1 was 5' end labeled with 32P using T4 polynucleotide kinase in a buffer containing 50 mM Tris*Cl pH 7.5, 10 mM MgCl$_2$, 0.1 mM spermidine 50 mM DTT, 3.3 pmol 32P-ATP and 20,000 units of T4 polynucleotide kinase. The 32P-BRALU1 was purified by ethanol precipitation.

32P-BRALU1 was then 3' end labeled with biotin by the following method. 32P-BRALU1 was allowed to hybridice with a complementary "sample DNA sequence" (a synthetic complementary single strand, a denatured whole genomic DNA sample known to contain a sequence complementary to BRALU1 (Chlamydia DNA), or a denatured whole genomic DNA sample not containing the complementary sequence (E. Coli). Once hybridized, and in the presence of bio-11dUTP and a DNA polymerase (preferably Taq polymerase), the 32P-BRALU1 will incorporate a single bio-11-dUTP onto its 3' end, if and only if, a complementary base is present at that location. This newly formed duplex was then heat denatured, cooled to allow the hybridization of unbiotinylated 32P-BRALU1 to the complementary DNA mentioned above, and then heated to an appropriate extension temperature to promote incorporation of bio-11-dUTP. This thermocycling process was repeated thirty times in order to amplify the 32P-biotinylated BRALU1 population. 32P-biotinylated BRALU1 was purified by ethanol precipitation.

The biotinylated product prepared from different sources (i.e. the synthetic complementary single strand, the denatured whole genomic DNA containing the complementary sequence) was immobilized onto streptavidin coated magnetic particles (Dynal). Once immobilized, the 32P-biotinylated BRALU1 was hybridized with a single stranded complementary oligonucleotide in 50 mM TrisHCl PH 8, 10 mM MgCl$_2$, 10 mM NaCl, 1 mM DTT, 50 µg/ml BSA. This immobilized duplex which contains the recognition site for the restriction endonuclease Alu I was digested with 5 units of Alu I for thirty minutes at 37° C. The magnetic particles were then separated from the digestion supernate, and this supernate was analyzed for released radioactivity by denaturing gel electrophoresis. Gel analysis shows (a) extension of the 32P-BRALU1 to create the biotinylated product occurs in a specific manner, limited by the complementarity of the hybridizing sequence and (b) this immobilized duplex can be digested with Alu I and can successfully release the 32P-labeled portion of the molecule into solution.

EXAMPLE 4

BRECL3 is a synthetic oligonucleotide, which contains a portion of the Chlamydia major outer membrane protein sequence but ends with an incomplete AG C recognition site of Alu I (see sequence). This molecule could then be extended in the 3' direction by four nucleotides in the manner stated previously, if provided with dTTP, dATP and a DNA polymerase. This process would create an enhanced population of oligonucleotide containing the full Alu I recognition sequence.

In a similar experiment in which 3' extended unlabeled BRECL3 is hybridized to an immobilized, radioactively labeled (32P), complementary sequence, and then digested with Alu I, the supernate would contain 32P labeled digestion product. However, by virtue of the specificity requirements of this extension process, BRECL3 molecules that can not be extended, can not act as substrates for Alu I digestion (i.e. no release of radioactively labeled digestion products into the supernate).

It will be appreciated that the instant specification and claims are set forth by way of illustration and that various modifications and changes may be made without departure from the spirit and scope of the present invention.

What is claimed is:

1. A process for detecting a nucleic acid sequence in a sample comprising:
    (1) treating said sample under hybridization conditions with an oligonucleotide that lacks the sequence AGCT;
    (2) extending the hybridization product from step (1) by adding polymerase and NTP's to create on the oligonucleotide strand the sequence AGCT;
    (3) treating the product of step (2) with labeled probe which is immobilized or immobilizable and which contains a recognition site for enzyme digestion that is completely or partially complementary to sequence AGCT on the oligonucleotide strand, under conditions that the oligonucleotide strand becomes hybridized to the labeled probe;
    (4) digesting the hybridization product of step (3) with Alu I restriction endonuclease; and
    (5) detecting the separated label which is released in solution,
the conditions being such that process step (4) automatically repeats itself.

* * * * *